US006893400B2

(12) United States Patent
Kawaguchi et al.

(10) Patent No.: US 6,893,400 B2
(45) Date of Patent: May 17, 2005

(54) ANGIOPATHY DIAGNOSING APPARATUS (75) Inventors: Osamu Kawaguchi, Nagoya (JP); Kiyoyuki Narimatsu, Komaki (JP)

(73) Assignee: Colin Corporation, Komaki (JP)

( * ) Notice: Subject to any disclaimer, the term of this patent is extended or adjusted under 35 U.S.C. 154(b) by 47 days.

(21) Appl. No.: 10/262,844

(22) Filed: Oct. 3, 2002

(65) Prior Publication Data

US 2003/0069508 A1 Apr. 10, 2003

(30) Foreign Application Priority Data

Oct. 10, 2001 (JP) ........................................ 2001-312208

(51) Int. Cl.[7] .................................................. A61B 5/02
(52) U.S. Cl. ...................................... 600/481; 600/504
(58) Field of Search ................................ 600/481–508, 600/300, 301

(56) References Cited

U.S. PATENT DOCUMENTS

| | | | | |
|---|---|---|---|---|
| 5,033,472 A | * | 7/1991 | Sato et al. ................... | 600/504 |
| 5,309,916 A | | 5/1994 | Hatschek | |
| 5,503,156 A | * | 4/1996 | Millar ......................... | 600/485 |
| 5,649,543 A | | 7/1997 | Hosaka et al. | |
| 6,379,309 B1 | * | 4/2002 | Ogura et al. ................ | 600/490 |
| RE37,852 E | * | 9/2002 | Aso et al. .................... | 600/485 |

FOREIGN PATENT DOCUMENTS

| | | |
|---|---|---|
| DE | 199 60 452 A1 | 8/2001 |
| EP | 1 050 267 A1 | 11/2000 |
| JP | A 52-146987 | 12/1977 |
| JP | B1 3027750 | 1/2000 |

* cited by examiner

Primary Examiner—Max F. Hindenburg
Assistant Examiner—Patricia Mallari
(74) Attorney, Agent, or Firm—Oliff & Berridge PLC (57) ABSTRACT

An apparatus for diagnosing an angiopathy of a living subject, including a first pulse-wave-propagation-velocity-related-information obtaining device which obtains a first pulse-wave-propagation-velocity-related information that is related to a first velocity at which a first pulse wave propagates through a first interval of the subject, a second pulse-wave-propagation-velocity-related-information obtaining device which obtains, at a substantially same time as a time when the first pulse-wave-propagation-velocity-related-information obtaining device obtains the first pulse-wave-propagation-velocity-related information, a second pulse-wave-propagation-velocity-related information that is related to a second velocity at which a second pulse wave propagates through a second interval of the subject that is different from the first interval, and a comparison-value calculating device for calculating a comparison value based on the first pulse-wave-propagation-velocity-related information and the second pulse-wave-propagation-velocity-related information.

6 Claims, 5 Drawing Sheets

ANGIOPATHY DIAGNOSING APPARATUS

BACKGROUND OF THE INVENTION

1. Field of the Invention

The present invention relates to an angiopathy diagnosing apparatus for diagnosing an angiopathy of a living subject, such as arteriosclerosis or arteriostenosis.

2. Related Art Statement

It is practiced to obtain, for diagnosing an angiopathy such as arteriosclerosis, arteriostenosis, aneurysm, or dissecting aneurysm, pulse-wave-propagation-velocity-related information that is related to a velocity at which a pulse wave propagates through an artery between two prescribed portions of a living subject; such as pulse-wave propagation velocity itself or pulse-wave propagation time. Since, for example, pulse-wave propagation velocity increases as arteriosclerosis advances, and conversely decreases as arteriostenosis advances, it is possible to diagnose those sorts of angiopathy based on the pulse-wave propagation velocity.

The pulse-wave-propagation-velocity-related information is also obtained for evaluating a therapeutic effect of an administered drug against arteriosclerosis or arteriostenosis. A device for obtaining pulse-wave-propagation-velocity-related information costs low, and enjoys an advantage that it can be easily used to obtain the information. Thus, this device is widely used.

Meanwhile, it is known that pulse-wave-propagation-velocity-related information is influenced by blood pressure of a living subject. Pulse-wave propagation velocity as a sort of pulse-wave-propagation-velocity-related information increases as subject's blood pressure increases, i.e., the former decreases as the latter decreases. Therefore, in order to accurately diagnose angiopathy based on pulse-wave-propagation-velocity-related information, it is needed to obtain the information when the subject shows a standard blood-pressure value. However, it is difficult to obtain, from the subject, every piece of pulse-wave-propagation-velocity-related information when the subject has the standard blood pressure. Hence, usually, it is practiced to measure, at a time of obtaining pulse-wave-propagation-velocity-related information, a blood pressure and make a rough diagnosis based on both the information and the blood pressure.

In addition, an MRI device (a magnetic-resonance imaging device) or a CT device (a computerized-tomography device) such as an X-ray CT device is known as a device capable of diagnosing angiopathy with high accuracy. Thus, if a patient is suspected of angiopathy, based on pulse-wave-propagation-velocity-related information, it is a common practice to make a final diagnosis using a CT device. However, since the accuracy of the diagnosis based on the pulse-wave-propagation-velocity-related information is not sufficiently high, a patient who, in fact, is free of angiopathy may be suspected of the disease based on the information, i.e., may be erroneously judged as needing a diagnosis using a CT device. On the other hand, each CT device is very expensive and accordingly a sufficient number of CT devices cannot be purchased. Thus, in many cases, patients must wait for their turns when they are judged as needing the CT inspection.

In addition, it is known that an upper-and-lower-limb blood-pressure measuring device can be used as a device capable of diagnosing arteriostenosis. For example, this device is disclosed in Japanese Patent No. 3,027,750 or its corresponding U.S. patent application Ser. No. 09/559,827. This upper-and-lower-limb blood-pressure measuring device includes two cuffs adapted to be worn on a superior limb (e.g., an upper arm) and an inferior limb (e.g., an ankle) of a living subject, respectively, measures superior-limb and inferior-limb blood-pressure values using the two cuffs, determines an index value by dividing the measured inferior-limb blood-pressure value by the measured superior-limb blood-pressure value, and diagnoses arteriostenosis based on the determined index value. However, the upper-and-lower-limb blood-pressure measuring device cannot diagnose arteriostenosis on the other body portions than the inferior limbs. In addition, this device cannot sufficiently accurately measure the inferior-limb blood-pressure values, and accordingly the reliability of the index values determined by the device is not sufficiently high. Moreover, this device needs a considerably long time to measure the blood-pressure values.

SUMMARY OF THE INVENTION

It is therefore an object of the present invention to provide an angiopathy diagnosing apparatus which can diagnose angiopathy, with high accuracy, based on pulse-wave-propagation-velocity-related information.

The Inventors have carried out extensive studies to achieve the above-indicated object, and found the following fact: If respective pieces of pulse-wave-propagation-velocity-related information are obtained from two different intervals of a living subject, at a substantially same time, it can be said that the two pieces of information are obtained from the two intervals, respectively, when the subject has a substantially same blood-pressure value. Here, providing that a comparison value is calculated based on the two pieces of information, it is found that a comparison value calculated based on the two pieces of information both of which are normal, differs from a comparison value calculated based on the two pieces of information one of which is normal but the other of which is abnormal. The present invention has been developed based on this finding.

The above object has been achieved by the present invention. According to the present invention, there is provided an apparatus for diagnosing an angiopathy of a living subject, comprising a first pulse-wave-propagation-velocity-related-information obtaining device which obtains a first pulse-wave-propagation-velocity-related information that is related to a first velocity at which a first pulse wave propagates through a first interval of the subject; a second pulse-wave-propagation-velocity-related-information obtaining device which obtains, at a substantially same time as a time when the first pulse-wave-propagation-velocity-related-information obtaining device obtains the first pulse-wave-propagation-velocity-related information, a second pulse-wave-propagation-velocity-related information that is related to a second velocity at which a second pulse wave propagates through a second interval of the subject that is different from the first interval; and a comparison-value calculating means for calculating a comparison value based on the first pulse-wave-propagation-velocity-related information and the second pulse-wave-propagation-velocity-related information.

According to this invention, the first pulse-wave-propagation-velocity-related-information obtaining device and the second pulse-wave-propagation-velocity-related-information obtaining device obtains, at a substantially same time, a first pulse-wave-propagation-velocity-related information at the first interval, and a second pulse-wavepropagation-velocity-related information at the second interval, respectively, and the comparison-value calculating means calculates a comparison value based on the first pulse-wave-propagation-velocity-related information and the second pulse-wave-propagation-velocity-related information. Although pulse-wave-propagation-velocity-related information changes in relation with blood pressure as well as angiopathy, the comparison value is calculated based on the two pieces of pulse-wave-propagation-velocity-related information obtained at the substantially same time, and accordingly the comparison value is free of the influence of change of the blood pressure. Thus, angiopathy can be diagnosed, with high accuracy, based on the comparison value. In addition, since pulse-wave propagation velocity can be measured between two arbitrary locations of the subject, angiopathy can be diagnosed on an arbitrary body portion of the subject other than an inferior limb of the subject. Moreover, since pulse-wave-propagation-velocity-related information can be easily obtained from even an inferior limb of the subject, angiopathy of the inferior limb can be diagnosed with high accuracy. Furthermore, since a piece of pulse-wave-propagation-velocity-related information can be obtained in synchronism with each heartbeat of the subject, a quick diagnosis can be made.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
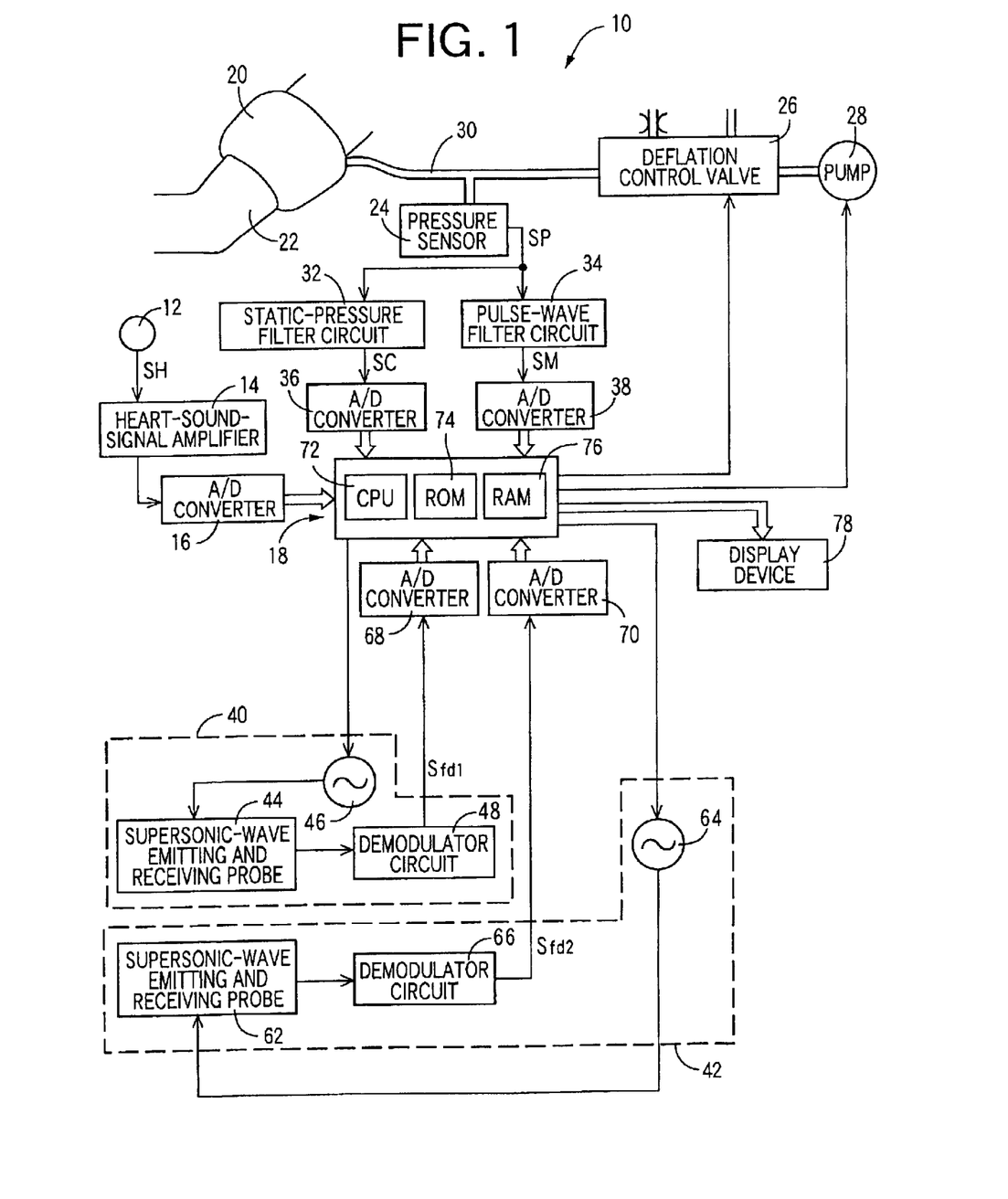
FIG. 1 is a view showing a construction of an angiopathy diagnosing apparatus to which the present invention is applied.

Hereinafter, there will be described in detail a preferred embodiment of the present invention, by reference to the drawings. FIG. 1 is a view showing a construction of an angiopathy diagnosing apparatus 10 to which the present invention is applied.

The present apparatus includes a heart-sound microphone 12 functioning as a first heartbeat-synchronous-signal detecting device. The microphone 12 is attached, with an adhesive tape, not shown, to a chest of a living subject, not shown. The microphone 12 is for detecting heart sounds as a heartbeat-synchronous signal produced from an upstream-side-end of a prescribed first interval of the subject. The microphone 12 incorporates a piezoelectric element, not shown, which converts the heart sounds produced from the heart of the subject, into an electric signal, i.e., heart-sound signal SH. A heart-sound-signal amplifier 14 includes four different filters, not shown, that attenuate, for clearly recording a high-pitched sound component of the heart sounds, a low-pitched sound component thereof having a high energy. The heart-sound signal SH amplified and filtered by the amplifier 14 is sent to an electronic control device 18 via an A/D (analog-to-digital) converter 16.

The present apparatus additionally includes a cuff 20 which includes a belt-like cloth bag and a rubber bag accommodated in the cloth bag and which is wound around, e.g., an upper portion 22 of a right arm of the subject. The cuff 20 is connected to a pressure sensor 24, a deflation control valve 26, and an air pump 28 via a piping 30. The deflation control valve 26 is selectively placed in a pressure-supply position in which the control valve 26 permits a pressurized air to be supplied from the air pump 28 to the cuff 20, a slow-deflation position in which the control valve 26 permits the pressurized air to be slowly discharged from the cuff 20, and a quick-deflation position in which the control valve 26 permits the pressurized air to be quickly discharged from the cuff 20.

The pressure sensor 14 detects an air pressure $P_K$ in the cuff 10, and supplies a pressure signal SP representing the detected pressure $P_K$, to each of a static-pressure filter circuit 32 and a pulse-wave filter circuit 34. The static-pressure filter circuit 32 includes a low-pass filter and extracts, from the pressure signal SP, a static-pressure component contained in the pressure signal SP, i.e., a cuff-pressure signal SC representing the static or pressing pressure in the cuff 20. The cuff-pressure signal SC is supplied to the control device 18 via an A/D converter 36. The pulse-wave filter circuit 34 includes a band-pass filter and extracts, from the pressure signal SP, an oscillating component, i.e., a cuff-pulse-wave signal SM. The cuff-pulse-wave signal SM is supplied to the control device 18 via an A/D converter 38. The cuff-pulse-wave signal SM represents an upper-arm pulse wave as a heartbeat-synchronous signal produced from the upper arm 22 in synchronism with heartbeat of the subject. The pulse-wave filter circuit 34 functions as an upper-arm-pulse-wave sensor as a second heartbeat-synchronous-signal detecting device. The upper-arm pulse wave is a heartbeat-synchronous signal that is produced from a downstream-side end of the first interval of the subject. Thus, the heart-sound microphone 12 as the first heartbeat-synchronous-signal detecting device, and the pulse-wave filter circuit 34 as the second heartbeat-synchronous-signal detecting device detect the heart sounds and the upper-arm pulse wave, respectively, from the heart and the upper arm as the upstream-side and downstream-side ends of the first interval of the subject, respectively.

The angiopathy diagnosing apparatus 10 includes, in addition to the heart-sound microphone 12 and the pulse-wave filter circuit 34, two heartbeat-synchronous-signal detecting devices, i.e., a first blood-flow-velocity measuring device 40 and a second blood-flow-velocity measuring device 42 functioning as a third and a fourth heartbeat-synchronous-signal detecting devices, respectively. The first blood-flow-velocity measuring device 40 includes a supersonic-wave emitting and receiving probe 44, an oscillator 46, and a demodulator circuit 48.

Figure 2:
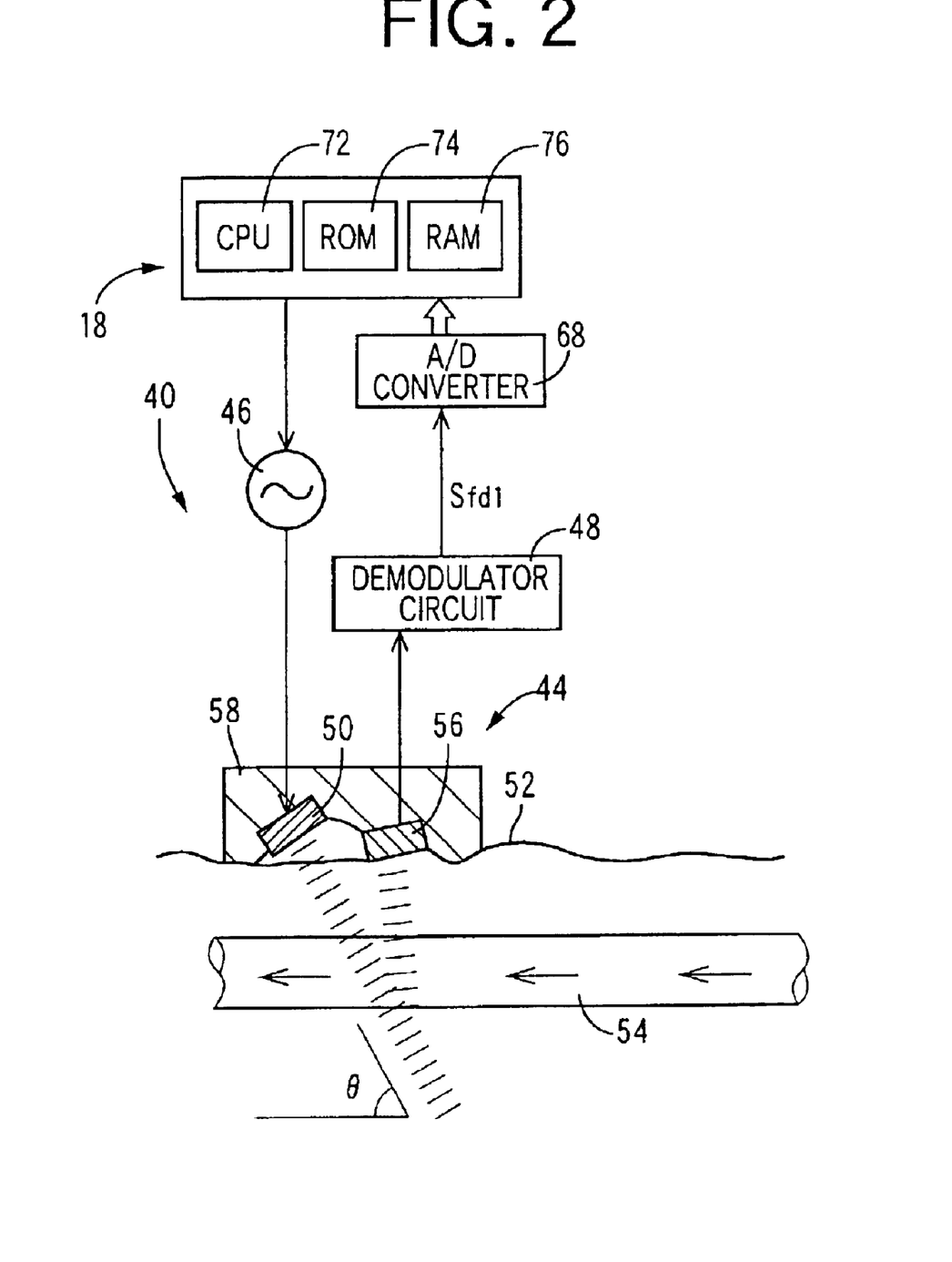
FIG. 2 is a view for explaining a construction of a supersonic-wave emitting and receiving device of the apparatus of FIG. 1.

FIG. 2 is a view for explaining a construction of the supersonic-wave emitting and receiving probe 44 which detects a femoral pulse wave as a heartbeat-synchronous signal produced from an upstream-side end of a prescribed second interval of the subject that is different from the above-described first interval. The probe 44 is worn on a body surface 52 of a femoral portion of the subject, such that the probe 44 is located at a position right above a prescribed artery, such as a femoral artery, of the subject. The probe 44 is identical with a probe that is employed in a well-known supersonic blood flow meter, and includes a generator 50 which generates a supersonic wave (i.e., an incident wave) having a prescribed frequency, fo; a piezoelectric element 56 which is held in close contact with the body surface 52 of the femoral portion and detects a reflected wave that is generated by the generator 50 and then is reflected from a blood flowing in an artery 54 running in the femoral portion; and a housing 58 which houses the generator 50 and the piezoelectric element 56. The probe 44 is detachably attached, with an attaching band, not shown, to the femoral portion such that a direction of arrangement of the generator 50 and the piezoelectric element 56 is parallel to a direction of running of the artery 54 and a direction of incidence of the supersonic wave generated by the generator 50 is opposite to a direction of flowing of the blood in the artery 54.

The piezoelectric element 56 supplies an electric signal representing the reflected wave detected thereby, to the demodulator circuit 48. The reflected wave contains a Doppler shift, fd1, (Hz) corresponding to a velocity at which the blood flows in the artery 54, and the demodulator circuit 48 extracts, from the electric signal supplied from the piezoelectric element 56, a Doppler-shift signal, Sfd1, representing the Doppler shift fd1 contained in the electric signal. The Doppler-shift signal Sfd1 extracted by the demodulator circuit 48 is supplied to the control device 18 via an A/D converter 68.

Back to FIG. 1, the second blood-flow-velocity measuring device 42 includes a supersonic-wave emitting and receiving probe 62, an oscillator 64, and a demodulator circuit 66 that have respective constructions identical with those of the counterparts of the first blood-flow-velocity measuring device 40. In order to detect a heartbeat-synchronous signal from a downstream-side end of the second interval of the subject, the supersonic-wave emitting and receiving probe 62 of the second blood-flow-velocity measuring device 42 is detachably attached, with an attaching band, not shown, to an ankle of a leg to the femoral portion of which the supersonic-wave emitting and receiving probe 44 of the first blood-flow-velocity measuring device 40 is attached, such that the probe 62 is located at a position right above a prescribed artery of the ankle, such as a posterior tibial artery. The probe 62 supplies, to the demodulator circuit 66, an electric signal containing a Doppler shift, fd2, corresponding to a velocity at which blood flows in the artery of the ankle, and the demodulator circuit 66 extracts, from the electric signal supplied from the probe 62, a Doppler-shift signal, Sfd2, representing the Doppler shift fd2 contained in the electric signal. The Doppler-shift signal Sfd2 extracted by the demodulator circuit 66 is supplied to the control device 18 via an A/D converter 70.

The control device 18 is provided by a so-called microcomputer including a CPU (central processing unit) 72, a ROM (read only memory) 74, a RAM 76, and an I/O port, not shown. The CPU 72 processes signals according to the control programs pre-stored in the ROM 74 by utilizing the temporary-storage function of the RAM 76, and generates respective drive signals via the I/O port to respective drive circuits, not shown, so as to control the deflation control valve 26 and the air pump 28. More specifically described, the CPU 72 controls the deflation control valve 26 and the air pump 28 so as to change and maintain the pressure in the cuff 20 to and at a pre-set pulse-wave-detect pressure, e.g., 60 mmHg which is sufficiently lower than a diastolic blood pressure of the subject and which assures that the cuff-pulse-wave signal SM extracted by the pulse-wave filter circuit 34 has a sufficiently high strength or voltage. In addition, the CPU 54 generates respective drive signals via the I/O port to control the oscillators 46, 64. In response to those drive signals, the oscillators 46, 64 supply, to the corresponding generators 50, respective signals having a prescribed frequency (e.g., 10 MHz). Moreover, the CPU 72 calculates a comparison value based on the signals supplied to the electronic device 18, and operates the display device 78 to display the thus calculated comparison value.

Figure 3:
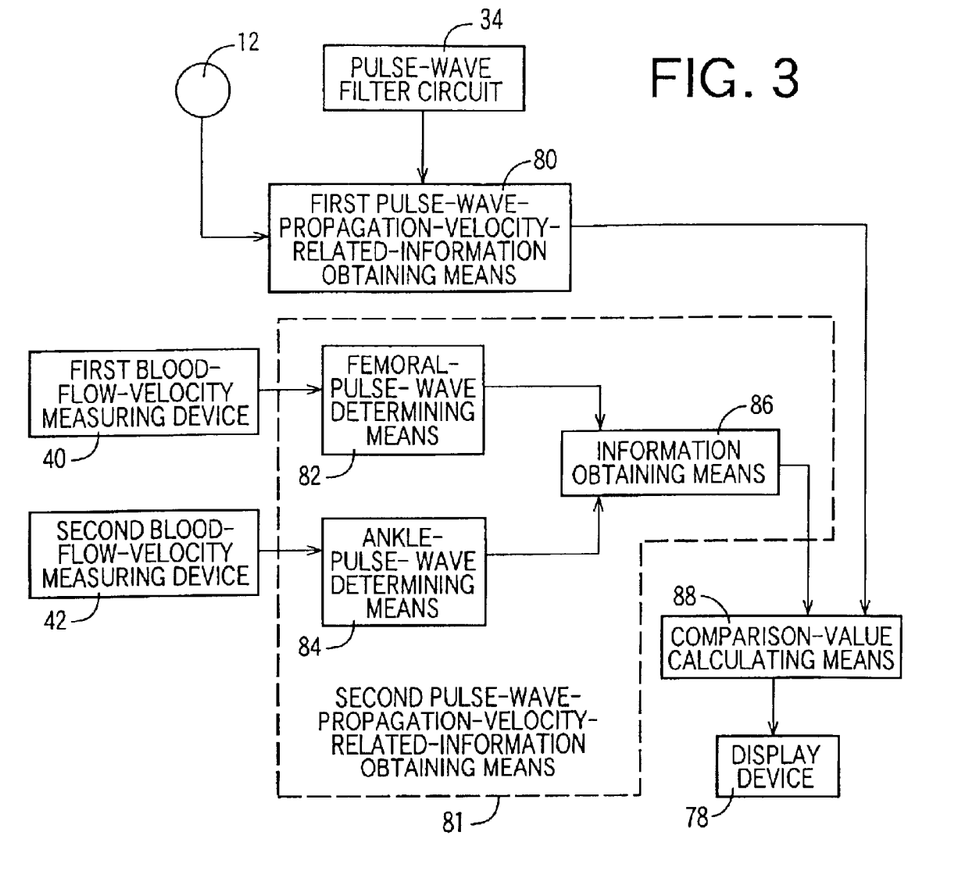
FIG. 3 is a block diagram for explaining essential control functions of a control device of the apparatus of FIG. 1.
Figure 5:
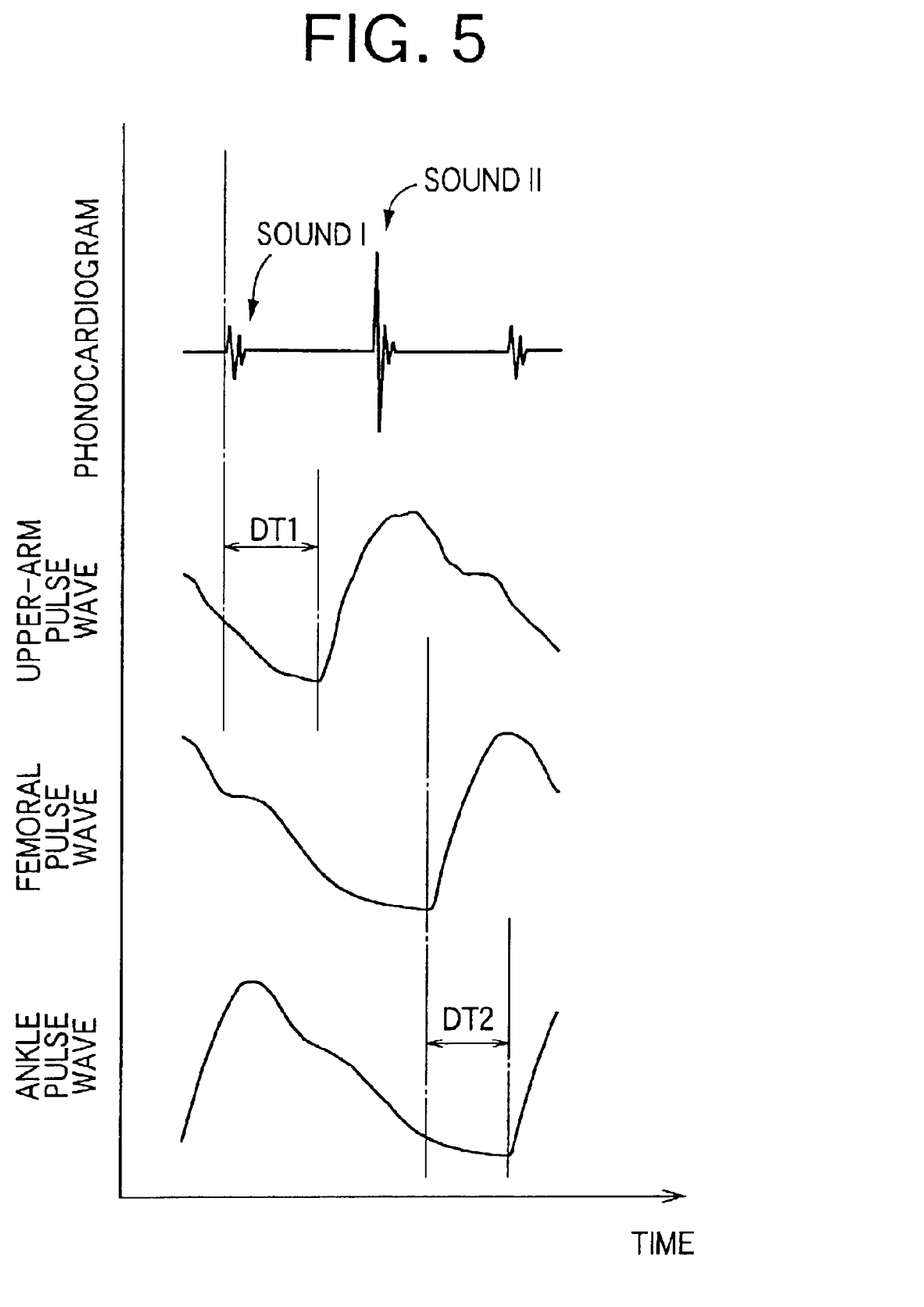
FIG. 5 is a graph showing a phonocardiogram, an upper-arm pulse wave, a femoral pulse wave, and an ankle pulse wave that are based on respective heartbeat-synchronous signals that are obtained while Steps S1 and S2 of FIG. 4 are repeated.

FIG. 3 is a block diagram showing essential control functions of the control device 18. A first pulse-wave-propagation-velocity-related-information obtaining means 80 reads in the heart sounds detected by the heart-sound microphone 12 and the upper-arm pulse wave extracted by the pulse-wave filter circuit 34, and obtains, based on the heart sounds and the upper-arm pulse wave, pulse-wave-propagation-velocity-related information at the above-indicated first interval. More specifically described, the first pulse-wave-propagation-velocity-related-information obtaining means 80 calculates, as a first pulse-wave propagation time DT1, a time difference between a prescribed point on a waveform of the heart sounds detected by the heart-sound microphone 12 and a prescribed point on a waveform of the upper-arm pulse wave detected by the pulse-wave filter circuit 34, as illustrated in FIG. 5. Alternatively, the first pulse-wave-propagation-velocity-related-information obtaining means 80 additionally calculates a first pulse-wave propagation velocity PWV1, based on the thus calculated first pulse-wave propagation time DT1, according to the following Expression 1, in which L1 is a distance from the subject's heart to the position where the cuff 20 is worn on the subject, and is replaced with a constant value that is experimentally obtained in advance:

$$PWV1 = L1/DT1 \qquad \text{(Expression 1)}$$

A second pulse-wave-propagation-velocity-related-information obtaining means 81 includes a femoral-pulse-wave determining means 82, an ankle-pulse-wave determining means 84, and an information obtaining means 86. The femoral-pulse-wave determining means 82 determines, based on the Doppler-shift signal Sfd1 supplied to the control device 18, the Doppler shift fd1 that changes with pulsation of the prescribed artery of the femoral portion, and determines a velocity V1 (cm/s) at which blood flows in the prescribed artery of the femoral portion, based on the thus determined Doppler shift fd1, according to the following Expression 2:

$$fd1 = f0(2 \times V1 \times \cos \theta1/C) \qquad \text{(Expression 2)}$$

where f0 is the frequency of the incident wave, C is sound velocity, and θ1 is the incidence angle of the incident wave and is replaced with a predetermined contact value.

The change of the thus determined blood flow velocity V1 is defined as a femoral pulse wave.

The ankle-pulse-wave determining means 84 determines, based on the Doppler-shift signal Sfd2 supplied to the control device 18, the Doppler shift fd2 that changes with pulsation of the prescribed artery of the ankle, and determines a velocity V2 (cm/s) at which blood flows in the prescribed artery of the ankle, based on the thus determined Doppler shift fd2, according to the following Expression 3:

$$fd2 = f0(2 \times V2 \times \cos \theta2/C) \qquad \text{(Expression 3)}$$

where f0 is the frequency of the incident wave, C is sound velocity, and θ2 is the incidence angle of the incident wave and is replaced with a predetermined contact value.

The change of the thus determined blood flow velocity V2 is defined as an ankle pulse wave.

The information obtaining means 86 obtains pulse-wave-propagation-velocity-related information at the above-described second interval, based on respective heartbeat-synchronous pulses of the femoral pulse wave and the ankle pulse wave that are determined by the femoral-pulse-wave determining means 82 and the ankle-pulse-wave determining means 84 at a substantially same time as the time when the first pulse-wave-propagation-velocity-related-information obtaining means 80 reads in the heartbeat-synchronous signals as illustrated in FIG. 5. More specifically described, the information obtaining means 86 calculates, as a second pulse-wave propagation time DT2, a time difference between a prescribed point on a waveform of the femoral pulse wave and a prescribed point on a waveform of the ankle pulse wave, the femoral and ankle pulse waves being detected at a substantially same time as the time when the heart sounds and the upper-arm pulse wave are read in for obtaining the first pulse-wave-propagation-velocity-related information. Alternatively, the information obtaining means 86 additionally calculates a second pulse-wave propagation velocity PWV2, based on the thus calculated second pulse-wave propagation time DT2, according to the following Expression 4, in which L2 is a distance from the position where the supersonic-wave emitting and receiving probe 44 is worn on the subject, to the position where the supersonic-wave emitting and receiving probe 62 is worn on the subject, and is replaced with a constant value that is experimentally obtained in advance:

$$PWV2=L2/DT2 \quad \text{(Expression 4)}$$

The expression "substantially same time" used in the description of the second pulse-wave-propagation-velocity-related-information obtaining means 81 means that a time difference between the time when the first pulse-wave-propagation-velocity-related-information obtaining means 80 reads in the heartbeat-synchronous signals and the time when the second pulse-wave-propagation-velocity-related-information obtaining means 81 determines the femoral pulse wave and the ankle pulse wave (the latter time can be regarded as the time when the means 81 reads in the Doppler shift signals Sfd1, Sfd2) is so short that change of the blood pressure of the subject during that time duration is negligible or permissible.

A comparison-value calculating means 88 calculates a comparison value based on the first pulse-wave-propagation-velocity-related information obtained by the first pulse-wave-propagation-velocity-related-information obtaining means 80 and the second pulse-wave-propagation-velocity-related information obtained by the second pulse-wave-propagation-velocity-related-information obtaining means 81, and operates the display device 78 to display the thus calculated comparison value. The comparison value may be any value indicating a degree of relativity between the first pulse-wave-propagation-velocity-related information and the second pulse-wave-propagation-velocity-related information. For example, in the case where pulse-wave propagation velocity PWV is measured as a sort of pulse-wave-propagation-velocity-related information, the comparison value may be a ratio R (R=PWV1/PWV2 or PWV2/PWV1) of one of the first pulse-wave propagation velocity PWV1 and the second pulse-wave propagation velocity PWV2 to the other of the two velocities; a difference d (d=PWV1−PWV2 or PWV2−PWV1) of the first pulse-wave propagation velocity PWV1 and the second pulse-wave propagation velocity PWV2; or a value obtained by dividing the difference d by the ratio R.

Figure 4:
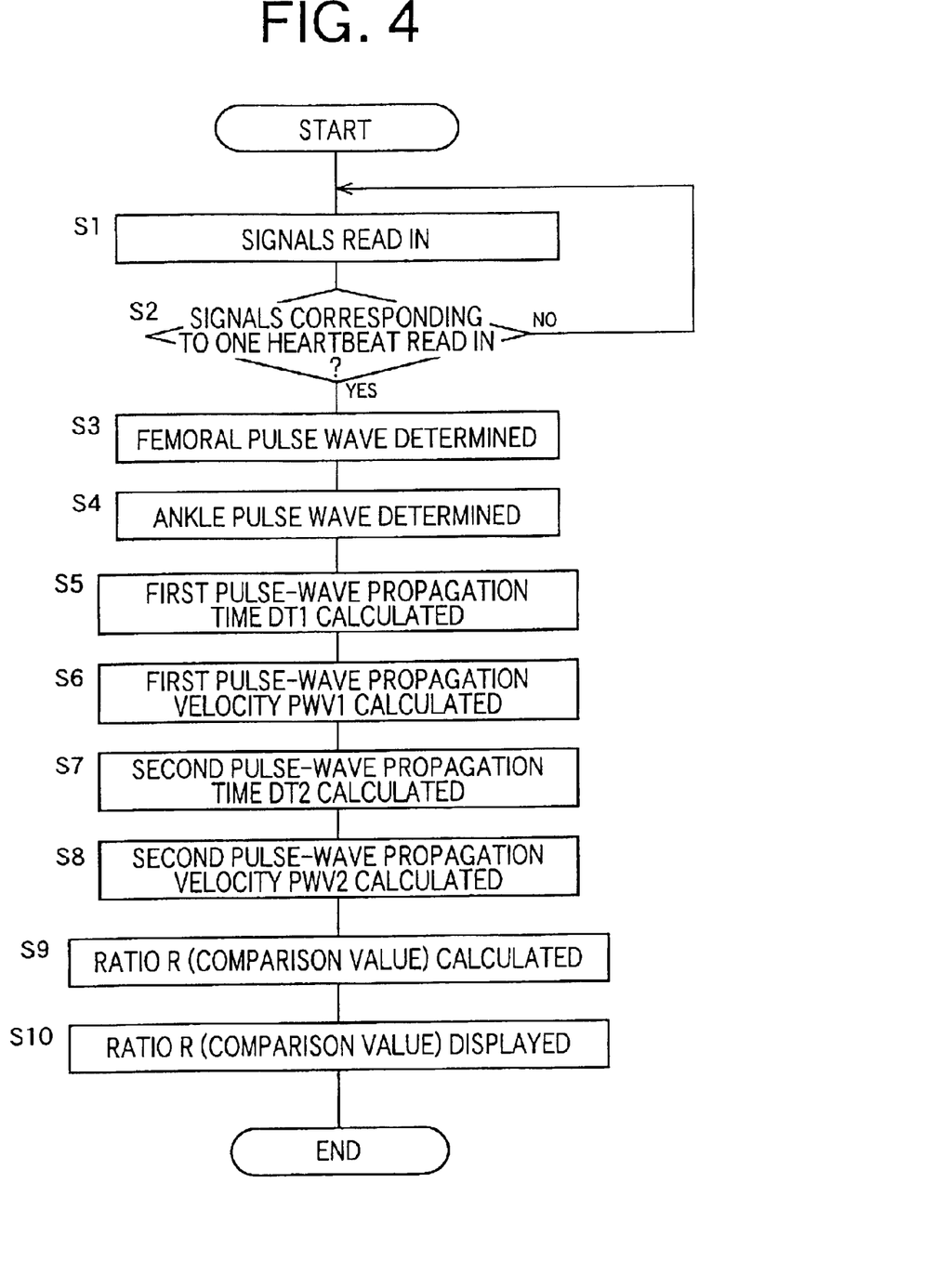
FIG. 4 is a flow chart representing the control functions of the control device, shown in FIG. 3.

FIG. 4 is a flow chart representing the control functions of the control device 18, shown in FIG. 3. Before the flow chart of FIG. 4 is implemented, the pressure in the cuff 20 is changed to, and is kept at, the above-described pulse-wave-detect pressure.

In FIG. 4, at Step S1 (hereinafter, "Step" is omitted, if appropriate), the control device 18 reads in the heart-sound signal SH, the cuff-pulse-wave signal SM, and the two Doppler-shift signals Sfd1, Sfd2. Then, at S2, the control device judges whether the control device has read in respective lengths of the above-indicated four heartbeat-synchronous signals that correspond to one heartbeat of the subject. If a negative judgment is made at S2, S1 and the following step is implemented again to continue reading in the heartbeat-synchronous signals. FIG. 5 is a graph showing a phonocardiogram, an upper-arm pulse wave, a femoral pulse wave, and an ankle pulse wave that are respectively based on the four heartbeat-synchronous signals read in while S1 and S2 are repeated.

Meanwhile, if a positive judgment is made at S2, the control goes to S3 corresponding to the femoral-pulse-wave determining means 82. At S3, the control device determines, based on the one-heartbeat length of the Doppler-shift signal Sfd1 read in while S1 and S2 are repeated, a change of a velocity V1 at which blood flows in the prescribed artery of the femoral portion, i.e., a femoral pulse wave, according to the above-indicated Expression 2. Then, the control goes to S4 corresponding to the ankle-pulse-wave determining means 84. At S4, the control device determines, based on the one-heartbeat length of the Doppler-shift signal Sfd2 read in while S1 and S2 are repeated, a change of a velocity V2 at which blood flows in the prescribed artery of the ankle, i.e., an ankle pulse wave, according to the above-indicated Expression 3.

Then, the control goes to S5 where, as illustrated in FIG. 5, the control device determines a start point of a first heart sound, I, on a waveform of the heat sounds read in while S1 and S2 are repeated, and additionally determines a rising point corresponding to the first heart sound I, on a waveform of the upper-arm pulse wave read in while S1 and S2 are repeated. Finally, the control device determines, as a first pulse-wave propagation time DT1, a time difference between the start point of the first heart sound I and the rising point of the upper-arm pulse wave. Subsequently, the control goes to S6 to determine a first pulse-wave propagation velocity PWV1 based on the thus determined first pulse-wave propagation time DT1 according to the above-indicated Expression 1. In the embodiment shown in FIG. 4, S1, S2, S5, and S6 corresponds to the first pulse-wave-propagation-velocity-related-information obtaining means 80.

Then, the control goes to S7 and S8 corresponding to the information obtaining means 86. At S7, as illustrated in FIG. 5, the control device determines a rising point on a waveform of the femoral pulse wave determined at S3, and additionally determines a rising point on a waveform of the ankle pulse wave determined at S4. Finally, the control device determines, as a second pulse-wave propagation time DT2, a time difference between the rising point of the femoral pulse wave and the rising point of the ankle pulse wave. Subsequently, the control goes to S8 to determine a second pulse-wave propagation velocity PWV2 based on the thus determined second pulse-wave propagation time DT2 according to the above-indicated Expression 4. In the embodiment shown in FIG. 4, S1 to S4, S7, and S8 corresponds to the second pulse-wave-propagation-velocity-related-information obtaining means 81.

Then, the control goes to S9 corresponding to the comparison-value determining means 88. At S9, the control device calculates a ratio R (=PWV2/PWV1) of the second pulse-wave-propagation velocity PWV2 determined at S8, to the first pulse-wave-propagation velocity PWV1 determined at S6. Subsequently, at S10, the control device operates the display device 78 to display the ratio R calculated at S9.

Since the ratio R is displayed on the display device 78, a medical staff such as a doctor or a nurse can diagnose an angiopathy of the subject, as follows: A normal range of the ratio R, i.e., a range of the ratio R that is obtained from the subject when both the respective arteries present in the first and second intervals are normal, is dependent on the manner in which the first and second intervals are prescribed, the age of the subject, etc. If an actually calculated ratio R is a value outside the normal range, it can be diagnosed that either one of the two arteries in the first and second intervals suffers an angiopathy. In this case, the single value R does not suffice for identifying which one of the two arteries in the first and second intervals suffers a disease. However, in the case where it is known beforehand that the artery in a specific one of the two intervals is normal, a single ratio R suffices for identifying whether the artery in the other interval suffers an angiopathy. More specifically described, if the ratio R is smaller than the normal range, it can be judged that the artery in the other interval suffers stenosis; and if the ratio R is greater than the normal range, it can be judged that the artery in the other interval suffers sclerosis.

In addition, in the case where a specific one of the first and second intervals is locally treated with, e.g., administration of a drug, a therapeutic effect of the treatment can be ascertained based on a time-wise change of the ratio R. Moreover, in the case where one of the first and second intervals is fixed on a body portion of the subject and the other interval is moved over a plurality of body portions of the subject so as to obtain a plurality of ratios R corresponding to the respective body portions, it is possible to identify which one of the respective arteries in those body portions suffers a disease. For example, if a greater number of ratios R are outside the normal range, than the number of the ratios R within the normal range, it can be judged that the artery in the fixed interval has a disease.

In the embodiment in accordance with the flow chart shown in FIG. 4, the control device obtains, at a substantially same time, the first pulse-wave propagation velocity PWV1 at the first interval, and the second pulse-wave propagation velocity PWV2 at the second interval, at Steps S1, S2, S5, and S6 (the first pulse-wave-propagation-velocity-related-information obtaining means 80), and Steps S1 to S4, S7, and S8 (the second pulse-wave-propagation-velocity-related-information obtaining means 81), and calculates the ratio R of the second pulse-wave propagation velocity PWV2 to the first pulse-wave propagation velocity PWV1, at Step S9 (the comparison-value calculating means 88). Though pulse-wave propagation velocity PWV changes in relation with blood pressure as well as angiopathy, the ratio R is calculated based on the first pulse-wave propagation velocity PWV1 and the second pulse-wave propagation velocity PWV2 obtained at a substantially same time, and accordingly the ratio R is free of the influence of change of the blood pressure. Thus, an angiopathy can be diagnosed, with high accuracy, based on the ratio R. In addition, since pulse-wave propagation velocity PWV can be measured between two arbitrary locations of the subject, an angiopathy can be diagnosed on an arbitrary body portion of the subject other than an inferior limb of the subject. Moreover, since pulse-wave propagation velocity PWV can be easily measured from even an inferior limb of the subject, an angiopathy of the inferior limb can be diagnosed with high accuracy. Furthermore, since pulse-wave propagation velocity PWV can be iteratively measured in synchronism with each heartbeat of the subject, a quick diagnosis can be made.

While the present invention has been described in its embodiment by reference to the drawings, the invention may otherwise be embodied.

For example, in the illustrated embodiment, the first interval is so prescribed as to extend from the subject's heart to the upper arm 22, and the second interval is so prescribed as to extend from the femoral portion to the ankle. However, it is possible to prescribed each of the first and second intervals on an arbitrary body portion of a living subject. For example, the first interval may be so prescribed as to extend from the subject's heart to the neck portion.

In addition, in the illustrated embodiment, the heart-sound microphone 12 is employed as the first heartbeat-synchronous-signal detecting device. However, an electrocardiograph for detecting an electrocardiogram may be employed as the first heartbeat-synchronous-signal detecting device, or the third heartbeat-synchronous-signal detecting device. Moreover, in the illustrated embodiment, the pulse-wave filter circuit 34 for extracting the pulse wave from the change of pressure in the cuff 20 is employed as the second heartbeat-synchronous-signal detecting device. However, like each of the third and fourth heartbeat-synchronous-signal detecting devices, a blood-flow-velocity measuring device may be employed as the second heartbeat-synchronous-signal detecting device. Contrarily, it is possible to wear a cuff at an upstream-side or downstream-side end of the second interval and employ, as the third or fourth heartbeat-synchronous-signal detecting device, a pulse-wave filter circuit for extracting a pulse wave from the change of pressure in the cuff. Moreover, each of the first to fourth heartbeat-synchronous-signal detecting devices may be provided by a photoelectric-pulse-wave detecting probe for measuring a blood oxygen saturation; a pressure-pulse-wave sensor which is adapted to be pressed against a prescribed artery, such as a radial artery, via skin and detects a pressure pulse wave from the artery; an impedance-pulse-wave sensor which detects an impedance of, e.g., an arm or a finger via electrodes; or a photoelectric-pulse-wave sensor which is adapted to be worn on, e.g., a free end portion of a finger and detects pulsation.

While the present invention has been described in detail in its embodiment by reference to the drawings, it is to be understood that the present invention is not limited to the details of the embodiment but may be embodied with other changes and improvements that may occur to a person skilled in the art.

What is claimed is:

1. An apparatus for diagnosing an angiopathy of a living subject, comprising:

a first pulse-wave-propagation-velocity-related-information obtaining device which obtains a first pulse-wave-propagation-velocity-related information that is related to a first velocity at which a first pulse wave propagates through a first interval of the subject;

a second pulse-wave-propagation-velocity-related-information obtaining device which obtains, at a substantially same time as a time when the first pulse-wave-propagation-velocity-related-information obtaining device obtains the first pulse-wave-propagation-velocity-related information, a second pulse-wave-propagation-velocity-related information that is related to a second velocity at which a second pulse wave propagates through a second interval of the subject that is different from the first interval;

a comparison-value calculating means for calculating a comparison value based on the first pulse-wave-propagation-velocity-related information and the second pulse-wave-propagation-velocity-related information; and a display device which displays the comparison value calculated by the comparison-value calculating means;

wherein the first pulse-wave-propagation-velocity-related-information obtaining device obtains, as the first pulse-wave-propagation-velocity-related information, the first velocity, and the second pulse-wave-propagation-velocity-related-information obtaining device obtains, as the second pulse-wave-propagation-velocity-related information, the second velocity, and wherein the comparison-value calculating means calculates, as the comparison value, at least one value selected from a difference obtained by subtracting one of the first and second velocities from the other of the first and second velocities, a ratio obtained by dividing one of the first and second velocities by the other of the first and second velocities, and a value obtained by dividing the difference by the ratio.

2. An apparatus for diagnosing an angiopathy of a living subject, comprising:

a first pulse-wave-propagation-velocity-related-information obtaining device which obtains a first pulse-wave-propagation-velocity-related information that is related to a first velocity at which a first pulse wave propagates through a first interval of the subject;

a second pulse-wave-propagation-velocity-related-information obtaining device which obtains, at a substantially same time as a time when the first pulse-wave-propagation-velocity-related-information obtaining device obtains the first pulse-wave-propagation-velocity-related information, a second pulse-wave-propagation-velocity-related information that is related to a second velocity at which a second pulse wave propagates through a second interval of the subject that is different from the first interval;

a comparison-value calculating means for calculating a comparison value based on the first pulse-wave-propagation-velocity-related information and the second pulse-wave-propagation-velocity-related information; and a display device which displays the comparison value calculated by the comparison-value calculating means;

wherein the first pulse-wave-propagation-velocity-related-information obtaining device obtains, as the first pulse-wave-propagation-velocity-related information, a first time needed for the first pulse wave to propagate through the first interval, and the second pulse-wave-propagation-velocity-related-information obtaining device obtains, as the second pulse-wave-propagation-velocity-related information, a second time needed for the second pulse wave to propagate through the second interval, and wherein the comparison-value calculating means calculates, as the comparison value, at least one value selected from a difference obtained by subtracting one of the first and second times from the other of the first and second times, a ratio obtained by dividing one of the first and second times by the other of the first and second times, and a value obtained by dividing the difference by the ratio.

3. An apparatus according to claim 2, wherein the second pulse-wave-propagation-velocity-related-information obtaining device comprises a femoral-pulse-wave detecting device which detects a femoral pulse wave of the subject.

4. An apparatus according to claim 3, wherein the second pulse-wave-propagation-velocity-related-information obtaining device comprises an ankle-pulse-wave detecting device which detects an ankle pulse wave of the subject, and determines the second time based on a time of detection of a prescribed periodic point of the femoral pulse wave and a time of detection of a prescribed periodic point of the ankle pulse wave.

5. An apparatus according to claim 2, wherein the first pulse-wave-propagation-velocity-related-information obtaining device comprises a heart-sound microphone which detects a heart sound of the subject.

6. An apparatus according to claim 5, wherein the first pulse-wave-propagation-velocity-related-information obtaining device comprises an inflatable cuff which detects an upper-arm pulse wave of the subject, and determines the first time based on a time of detection of a prescribed periodic point of the heart sound and a time of detection of a prescribed periodic point of the upper-arm pulse wave.

* * * * *